Figure 1:
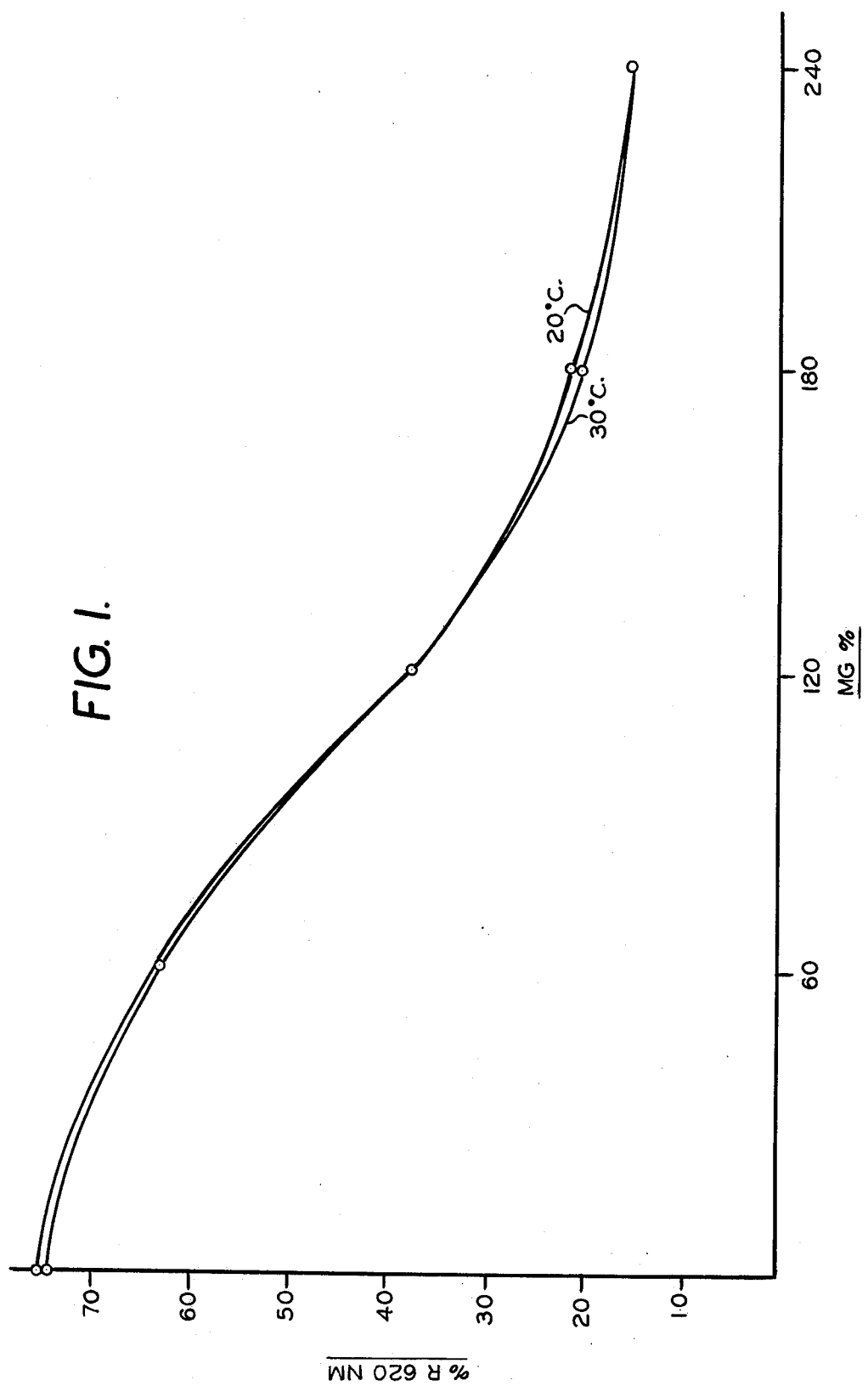

United States Patent [19]

Werner et al.

[11] 3,947,377

[45] Mar. 30, 1976

[54] STABILIZED INDICATOR COMPOSITIONS CONTAINING 9-γ-AMINOPROPYL)-3-AMINOCARBAZOLE

[75] Inventors: Wolfgang Werner, Mannheim-Vogelstang; Peter Vogel, Weinheim; Hugo Tiedemann, Mannheim-Wallstadt; Werner Guthlein, Mannheim-Neckarau, all of Germany

[73] Assignee: Boehringer Mannheim GmbH, Mannheim, Germany

[22] Filed: Sept. 24, 1973

[21] Appl. No.: 399,885

Related U.S. Application Data

[62] Division of Ser. No. 326,205, Jan. 24, 1973, Pat. No. 3,822,285.

[30] Foreign Application Priority Data

Feb. 8, 1972  Germany............................ 2205733

[52] U.S. Cl................................ 252/408; 23/230 B
[51] Int. Cl.² C09K 3/00; G01N 31/00; G01N 33/00
[58] Field of Search..................... 252/408; 260/315; 23/230 B

[56] References Cited

UNITED STATES PATENTS

| | | | |
|---|---|---|---|
| 3,350,278 | 10/1967 | Gretton et al. | 252/408 |
| 3,615,228 | 10/1971 | Thiegs | 252/408 |
| 3,778,384 | 12/1973 | Dooley | 252/408 |
| 3,792,044 | 2/1974 | Dooley | 252/408 |
| 3,822,285 | 7/1974 | Werner et al. | 260/315 |

*Primary Examiner*—Benjamin R. Padgett
*Assistant Examiner*—Josephine Lloyd
*Attorney, Agent, or Firm*—Burgess, Dinklage & Sprung

[57] ABSTRACT

9-(γ-aminopropyl)-3-aminocarbazole, when incorporated into indicator compositions also comprising oxidation indicators such as o-tolidine for the enzymatic detection of glucose, results in outstandingly stable indicator compositions and not adversely effected by normally interfering components in the test sample.

12 Claims, 2 Drawing Figures

FIG. I.

STABILIZED INDICATOR COMPOSITIONS CONTAINING 9-(γ-AMINOPROPYL)-3-AMINOCARBAZOLE

This is a division of application Ser. No. 326,205, filed Jan. 24, 1973, now U.S. Pat. No. 3,822,285.

The present invention is concerned with a new carbazole compound, with the preparation thereof and with test devices containing them.

For quite a long time, glucose has been determined quantitatively in body fluids by an enzymatic test reaction in which the glucose is oxidized to gluconic acid by means of glucose oxidase and atmospheric oxygen. The hydrogen peroxide liberated by this reaction reacts, by means of peroxidase, with a chromogen which should be as colorless as possible. The extinction of the colored material which thereby develops provides a measure of the amount of glucose present in the fluid being investigated. Since the reactions carried out in test tubes and in cuvettes can only be evaluated by means of expensive apparatus and trained personnel, in recent years test strips have been developed which contain the necessary reagents in the correct amounts and which develop a color reaction directly upon the reagent carrier, after moistening with the fluid being investigated. Such test strips can comprise an absorbent carrier, for example of filter paper, but according to U.S. Pat. No. 3,630,957, it is also possible to incorporate the reagents into a water-resistant film. These test films can be wiped off and are, therefore, especially suitable for the investigation of cloudy liquids, for example of blood.

Recently, endeavors have been made to improve the semiquantitative evaluations of test strips with color tables, by optically measuring the test strips after the detection reaction has taken place. For this purpose, relatively simple remission photometers have been developed which enable a quantitative evaluation of the test films to be carried out.

In the development of test films, it has been found that the detection reactions are, to a considerable extent, dependent upon the temperature so that it was scarcely possible, without having regard to the temperature conditions, to obtain reproducible results. This is especially disturbing in a remission photometer because the light beam used for the measurement rapidly heats up the reaction zone of the test strip.

A mixture of the oxidation indicators o-tolidine and 3-amino-9-ethyl-carbazole has previously been used as the chromogen for test films. This mixture has proved to be very useful because of its especially favorable color change from red to green, but it suffers from the above-mentioned disadvantage of being very temperature-dependent.

Hitherto, in spite of intensive investigations, no indicators have been found which give temperature-independent and reproducible color values. On the contrary, depending upon the reaction temperature and also upon the temperature at which the test strips are read off, color variations occur which, in some cases, can considerably falsify the results obtained. In the case of temperature variations such as occur in the case of evaluations using a remission photometer, test films for the determination of glucose in blood have, for the above-mentioned reasons, been useless.

We have now found that 9-(γ-aminopropyl)-3-aminocarbazole, which is a new compound, is an indicator for the enzymatic detection of glucose which, together with other oxidation indicators, especially with o-tolidine, gives color values depending upon the glucose concentration of a liquid to be tested which are, within wide limits, independent of temperature and thus gives reproducible color values.

Thus, the instant invention provides a new compound, viz., 9-(γ-aminopropyl)-3-aminocarbazole and indicator compositions comprising it.

In addition to the temperature-independence, this new indicator possesses a further valuable and surprising property, which considerably extends its usefulness in test devices: we have found that this new indicator is not influenced by disturbing components present, for example, in urine so that it is now possible to carry out quantitative determinations of glucose in urine by means of test devices. The previously known test devices which were based on the principle of an enzymatic glucose determination according to the glucose oxidase/peroxidase method, usually contained o-tolidine as indicator and were considerably disturbed not only by certain frequently occurring and known components of urine, for example, acetoacetic acid or ascorbic acid, but also by many unknown substances present in urine. Thus, although it was possible to make a qualitative or, at best, semi-quantitative assessment of the glucose concentration, a dependable quantitative evaluation was not possible. Test devices for the determination of glucose in urine with the new indicator according to the present invention show, in the most varied kinds of urine (pH, accompanying materials, protein content and the like), the same reaction colors with the same glucose contents. This discovery was not to have been foreseen and provides a urine diagnostic of great practical value.

For the production of temperature-independent test films, the test reagents can be mixed, for example, in the manner described in German Patent Specification No. 1,598,153, with a synthetic resin dispersion, for example, with polyvinyl acetate propionate co-polymers (Propiofan 70 D), and sodium alginate (Algipon) added thereto as a thickening agent or swelling agent. As further additives, it has proved useful to use an anion-active wetting agent, for example sodium nonyl sulfate, or a technical mixture of organic sulfonates (Texapon P) and ammonium perfluorooctanoate.

As buffer, it is particularly preferred to use a phosphate buffer with a pH range of 5-8, and preferably of 5.5-7.0, or a citrate buffer or other conventional buffer which give the above-mentioned pH range.

The following Table gives a summary of several formulations by means of which there can be obtained a temperature-independent color reaction in the case of glucose test films. In this Table, the amounts given refer to 100 g of coating mass:

TABLE I

| component | lower limit | upper limit | preferred amount |
|---|---|---|---|
| synthetic resin dispersion | 20 g | 80 g | 40 – 50 g |
| swelling agent | 0.1 g | 2.0 g | 0.5 – 0.6 g |
| wetting agent | 0.1 g | 2.0 g | 0.5 – 1.0 g |
| buffer | 0.5 g | 5.0 g | 2.5 – 3.5 g |
| glucose oxidase | $10^2$ U | $10^5$ U | $10^3 – 10^4$ U |
| peroxidase | $10^2$ U | $10^5$ U | $10^3 – 10^4$ U |
| o-tolidine | 0.1 g | 1.0 g | 0.2 – 0.7 g |
| indicator I* | 0.01 g | 0.5 g | 0.02 – 0.03 g |

*Indicator I = 9-(γ-aminopropyl)-3-aminocarbazole

The test films are produced in the following manner: to the synthetic resin dispersion are added the other components, dissolved in water, but with the exception of Indicator I and of the o-tolidine, which are dissolved in methanol or acetone. The dispersion is well mixed, then applied to a non-absorbent substrate in a layer thickness of 100 – 500 μ, and preferably of 300 – 400 μ, and dried in a current of warm air. The dispersion can be applied, for example, in the form of a strip onto a stiff synthetic resin film. This is then cut transversely so that rectangular synthetic strips are obtained, the lower ends of which contain the reactive test layer.

However, a water-impermeable, coated paper or a thin film can be surface-coated with the reagent mass. The surface thus coated is then cut up into narrow strips which can then be sealed or stuck onto the lower edge of foil bands, which are then cut transversely in the manner described above. The last-mentioned method has the advantage of requiring a much shorter coating time.

The test strips thus produced can be used, according to German Patent Specification No. 1,598,153, for the detection of glucose in whole blood, a color change hereby taking place from red via olive colors to green. Because of the temperature independence of their colors, the test strips are especially suitable for evaluation in a remission photometer, for example of the kind described in German Patent Specification No. 2,056,352.

Test papers for the determination of glucose in urine are, in analogy to the strips already known (cf. German Patent Specification No. 1,546,307) produced by the impregnation of absorbent carriers, for example filter paper or blotting paper, with the reagents.

The following Table II gives a summary of some formulations which can be used for the production of test papers, the amounts given referring to 100 ml of impregnation solution:

TABLE II

| component | lower limit | upper limit | preferred amount |
| --- | --- | --- | --- |
| glucose oxidase | $10^3$ U | $10^5$ U | $2 - 4 \times 10^4$ U |
| peroxidase | $10^2$ U | $10^5$ U | $3 - 5 \times 10^3$ U |
| buffer | 0.01 M | 0.1 M | 0.025 – 0.05 M |
| wetting agent | 0 | 2 g | 0.1 – 0.2 g |
| thickening agent | 0 | 5 g | 0.1 – 0.5 g |
| indicator I | 0.5 g | 10 g | 5 – 7 g |

The buffer used can be, for example, a phosphate or citrate buffer with a pH of 4.5 – 7, and preferably of 5 – 6.

As wetting agent, there can be used not only a non-ionic agent (for example, polyoxyethylene sorbitan mono-laurate) but also an anionic agent (for example dioctyl sodium sulfosuccinate, sodium lauryl sulfate or ammonium perfluorooctanoate).

As thickening agents, there can be used, for example polyvinyl pyrrolidones, but alginates, gelatines and similar materials can also be employed.

The components are dissolved in appropriate solvents, usually in a mixture of water and ethanol. Filter paper is impregnated with this solution and thereafter dried. However, the water-soluble components, for example buffer, enzymes, wetting agents and thickening agents, can be applied in one step and the indicators in a separate step. The impregnated test papers can be cut up into narrow strips and sealed between two synthetic resin films or between a synthetic resin film and a fine-mesh material. The test papers are briefly dipped into the urine to be investigated and, after a certain period of time, compared with a color comparison scale. In the case of comparatively low glucose concentrations, the test papers are read off after 0.5 – 1 minute and, in the case of high glucose concentrations, after 3 – 5 minutes. However, as already described, the color can also be measured with a remission photometer or with a simple test strip photometer.

The exactitude of the above-described test films and test papers fully satisfies the requirements for practical and clinical investigations.

Thus, according to the present invention, there is provided, as a new compound, 9-(γ-aminopropyl)-3-aminocarbazole, which has the formula:

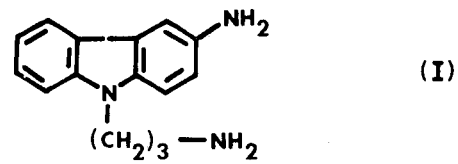

(I)

as well as the salts thereof, with inorganic and organic acids.

The present invention also provides test devices, for example test strips and test films, with a content of (γ-aminopropyl)-3-aminocarbazole and/or of at least one salt thereof.

The above-mentioned new 9-(γ-aminopropyl)-3-aminocarbazole can be prepared, for example, according to one of the following methods.

1. A compound of the general formula:

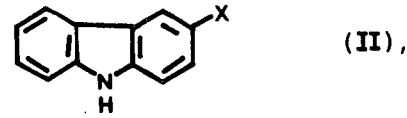

(II), wherein X is a hydrogen atom, a free or acylated amino group or a nitro group;

a. is reacted with acrylonitrile and, when X is a hydrogen atom, is nitrated and the cyano group, as well as the nitro group when present, reduced to an amine group and an acylated amino group, when present, is deacylated; or b. when X is a nitro group, the N-H acid compound is converted into an alkali metal or quaternary ammonium salt and then reacted with a compound of the general formula:

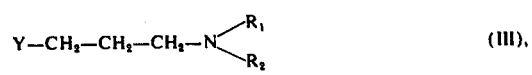

(III), wherein Y is a reactive ester group and $R_1$ and $R_2$, which may be the same or different, are conventional protective groups for the amino function, and subsequently, in any desired sequence, the nitro group is reduced to an amino group and the protective groups $R_1$ and $R_2$ are split off; or 2. a compound of the general formula:

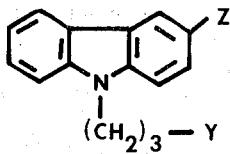

(IV), wherein Y has the same meaning as above and Z is a free or acylated amino group, is reacted with ammonia and, if necessary, Z is subsequently deacylated; whereafter, the compound (I) obtained is, if desired, converted into a salt by reaction with an inorganic or organic acid.

An amino group present in the 3-position of the carbazole system can be acylated with aliphatic or aromatic radicals, and preferably with alkanoyl radicals containing 2-6carbon atoms, the acetyl radical being especially preferred.

The reaction of the compounds of general formula (II) with acrylonitrile can be carried out in the presence of a basic catalyst, for example of benzyl trimethyl ammonium hydroxide, in an inert solvent, for example benzene. If X is a hydrogen atom, the compound can be nitrated with nitric acid in glacial acetic acid. Not only the nitro group in the 3-position, but also the nitrile group in the side chain, can be catalytically hydrogenated, for example, in the presence of Raney nickel. An acyl radical possibly present on the 3-amino group can be simply split off by heating in an aqueous mineral acid. In this manner, with hydrochloric acid there is obtained directly the dihydrochloride, which is preferred because of its storage stability.

As alkali metal salts of 3-nitrocarbazole, from the practical point of view, only the sodium or potassium salts are to be considered. However, salts with strongly basic quaternary ammonium bases can also be used. The salts are formed upon dissolving 3-nitrocarbazole in an alcoholic solution of the base in question.

Preferred reactive ester groups Y are, in particular, the chlorides and bromides; however, alkyl sulfonates, tosylates, brosylates and similar reactive esters can also be used.

As radicals $R_1$ and $R_2$, there can be used all of the groups usual for the protection of amino groups, for example acyl radicals, especially acetyl radicals, as well as the bifunctional phthaloyl radical; in the latter case, the subsequent splitting off of the protective group can be carried out especially simply with hydrazine. When X is a nitro group, the phthaloyl radical can be split off, together with the reduction of the nitro group, in a one-pot process by boiling with hydrazine and subsequently adding Raney nickel in aqueous solution. Acyl radicals can be split off in the usual manner with the use of dilute mineral acids.

The compounds of general formula (IV) can be prepared, for example, by the reaction of 3-nitrocarbazole with a 1,3-dihalopropane, for example with 1-bromo-3-chloropropane, followed by hydrogenation in the presence of Raney nickel. However, the reaction is not limited to halides. On the contrary, the reaction can also be carried out with, for example, 1-chloropropane 3-ethyl sulfonate and similar compounds.

The reaction with ammonia, which can be carried out in aqueous solution at an elevated temperature, leads to the compound (I) which, if desired, can be converted into a simple or double salt by reaction with an inorganic or organic acid.

As acid, there can be used, for example, hydrochloric acid, sulfuric acid, phosphoric acid, hydrobromic acid, boric acid, acetic acid, oxalic acid, lactic acid, citric acid, malic acid, benzoic acid, malonic acid, maleic acid, succinic acid, butyric acid or propionic acid.

The following Examples are given for the purpose of illustrating the present invention:

Example 1

Preparation of 9-(γ-aminopropyl)-3-aminocarbazole dihydrochloride.

11.7 g 9-(β-cyanoethyl)-3-nitrocarbazole in 50 ml dioxan and 75 ml 5N methanolic ammonia were hydrogenated, in the presence of 4.5 g Raney nickel, for six hours, at 110°C and a hydrogen pressure of 65 atmospheres in an M-R autoclave. After removing the catalyst by suction filtration and evaporation of the solvent, there were obtained 12 g of a brown oil. This was dissolved in 50 ml methanol and treated several times with charcoal at an elevated temperature. The filtrate was cooled and 35 ml 8.5N ethereal hydrochloric acid were added thereto dropwise, while cooling with ice. The crystals formed were filtered off with suction and washed with ether. There were obtained 11.6 g (84.2% of theory) of yellowish-green dihydrochloride. For the purpose of purification, this was clarified in 50 ml water at an elevated temperature by adding charcoal, then filtered with suction and the filtrate evaporated. After again recrystallizing from methanol and a little water, there were obtained 9.7 g (70.2% of theory) 9-(γ-aminopropyl)-3-aminocarbazole dihydrochloride in the form of colorless crystals which melt, with decomposition, at 290°C.

The 9-(β-cyanoethyl)-3-nitrocarbazole used as starting materials were obtained in the following manner:
Variant A:

66.8 g (0.4 mol) carbazole were suspended in a mixture of 100 ml (1.66 mol) acrylonitrile and 250 ml benzene in a 1000 ml three-necked flask equipped with a stirrer, condenser, thermometer and dropping funnel, then heated to 60°C, while stirring, and mixed with a few drops of a 40% aqueous solution of benzyl trimethyl ammonium hydroxide. The reaction mixture was heated to 78°C, with considerable foaming. It was further stirred for 45 minutes at this temperature, the carbazole thereby going completely into solution. After evaporation of the solvent and of excess acrylonitrile, the crude 9-(β-cyanoethyl)-carbazole was recrystallized from acetone. There were obtained 75.1 g (85.3% of theory) of the desired compound in the form of beige-colored crystals with a melting point of 154°C (lit. 155°–156°C). The compound was chromatographically uniform.

17.9 g (0.08 mol) of the 9-(β-cyanoethyl)-carbazole thus obtained were suspended in 108 ml glacial acetic acid in a three-necked flask equipped with a stirrer, condenser, thermometer and dropping funnel and a mixture of 13.5 ml glacial acetic acid and 6.75 ml 65% nitric acid were added dropwise, while stirring, at 80°C, the nitrile thereby going into solution. The reaction mixture was further stirred for 15 minutes at 80°C, cooled and thereafter added dropwise into 200 ml ice water. The precipitated nitro compound was filtered off with suction, washed with a little water and the crude product recyrstallized from acetone. There were obtained 17.2 g (79.9% of theory) 9-(β-cyanoethyl)-3- nitrocarbazole in the form of yellow-green crystals with a melting point of 225°C.

Variant B:

21.2 g (0.1 mol) 3-nitrocarbazole were suspended in 250 ml benzene in a three-necked flask equipped with stirrer, condenser and thermometer and present in an oil-bath, then mixed with 50 ml acrylonitrile, heated to 50°C and, after the addition of two drops of benzyl trimethyl ammonium hydroxide, reacted for two hours at 70°C, while stirring. After evaporation of the reaction mixture and recrystallization of the residue from aqueous acetone, there were obtained 22 g 9-($\beta$-cyanoethyl)-3-nitrocarbazole, which was further worked up directly.

Example 2

Test film for the detection of glucose in blood.

Components:

| | | |
|---|---|---|
| polyvinyl acetate propionate dispersion (Propiofan 70 D) | | 45.0 g |
| 1.85% solution of sodium alginate in 0.5M phosphate buffer of pH 5.5 | | 35.0 g |
| organic sodium sulfonate (Texapon P) | | 1.0 g |
| glucose oxidase (104 U/mg) | dissolved in 10 ml water | 0.114 g |
| peroxidase (63.1 U/mg | | 0.128 g |
| o-tolidine | | 0.2 g |
| 9-($\gamma$-aminopropyl)-3-aminocarbazole | dissolved in 6 ml methanol | 0.026 g |

The components were well mixed, coated with a layer thickness of 300 $\mu$ onto a film of polyvinyl chloride and dried at 60°C for 35 minutes. When a drop of glucose-containing blood was applied to the coated film and then wiped off after 1 minute, then, after further 2 minutes, the following temperature-independent reaction colors were observed:

| | |
|---|---|
| 60 mg % glucose | brownish-red |
| 120 mg % glucose | olive |
| 180 mg % glucose and more | green with increasing color depth |

FIG. 1 of the accompanying drawings shows the calibration curves measured with a commercially available remission photometer at 20°C and 30°C.

Figure 2:
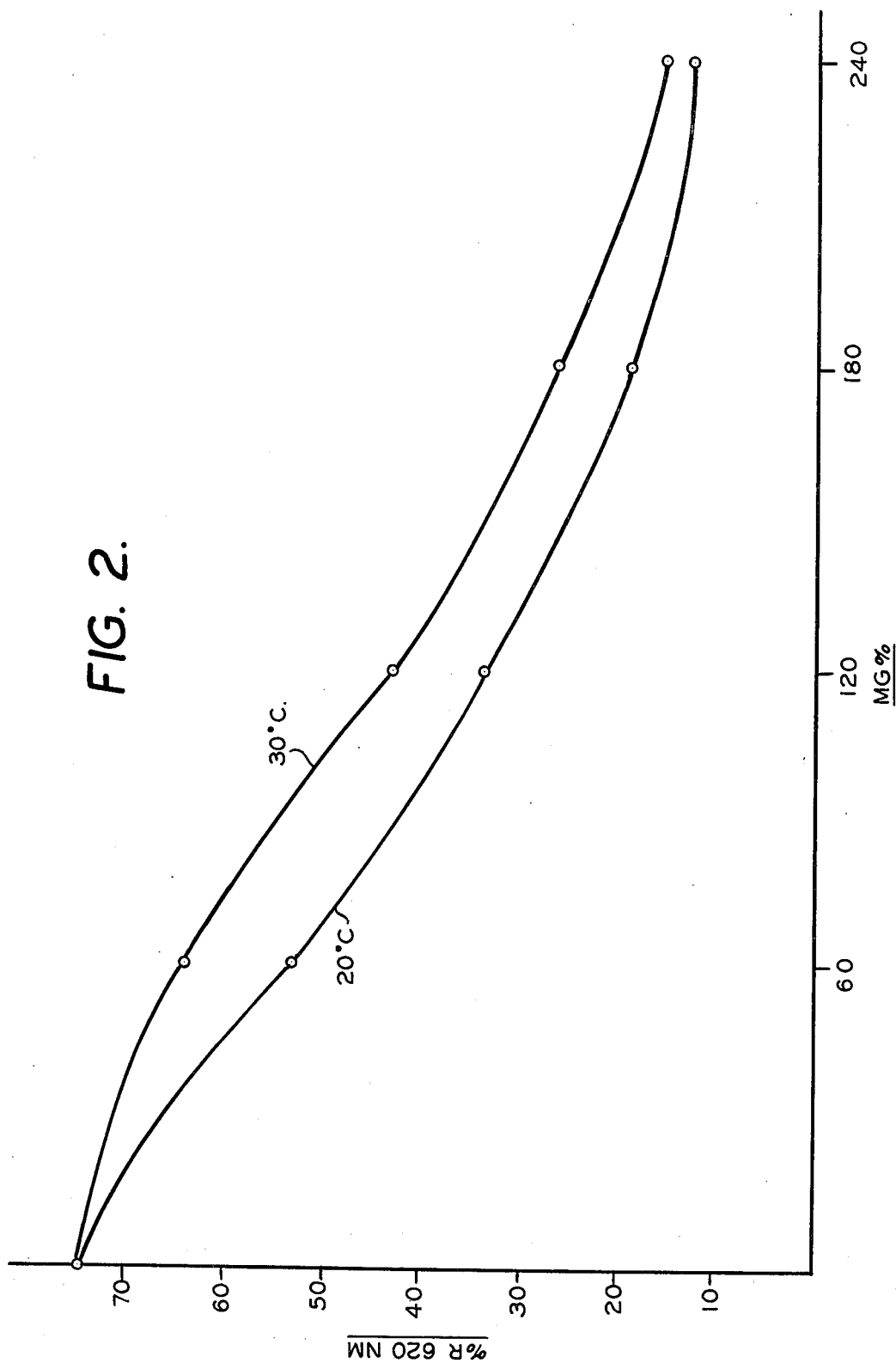

A test film of the same composition and produced in the same manner but which, instead of containing 0.026 g 9-($\gamma$-aminopropyl)-3-aminocarbazole, contained 0.04 g 9-ethyl-3-amino carbazole, showed practically the same reaction colors which were, however, temperature-dependent and, therefore, not reproducible. FIG. 2 of the accompanying drawings showed that there was a considerable difference between the calibration curves obtained at 20° and 30°C.

Example 3

Test film for the detection of glucose in blood.

Components:

| | | |
|---|---|---|
| polyvinyl acetate propionate dispersion (Propiofan 70 D) | increase- | 45.0 g |
| 1.85% solution of sodium alginate in 0.5M phosphate buffer of pH 5.5 | | 35.0 g |
| sodium nonyl sulfate dissolved in 5.0 ml water | | 0.75 g |
| glucose oxidase (62.7 U/mg) | dissolved in 10 ml water | 0.189 g |
| peroxidase (68.8 U/mg) | | 0.235 g |
| o-tolidine dissolved in 2.5 ml acetone | | 0.6 g |
| 9-($\gamma$-aminopropyl)-3-aminocarbazole dihydrochloride dissolved in 2.5 ml water | | 0.026 g |

The components were well mixed, applied in a layer thickness of 310 $\mu$ to a polyvinylidene chloride-coated paper and dried for 35 minutes at 60°C. The test paper thus obtained was used in the manner described in Example 2. The calibration curves measured with a remission photometer at 20°C and 30°C did not show any substantial deviations.

The reaction colors obtained with the test strip were as follows:

| | |
|---|---|
| 60 mg % glucose | pink-ochre |
| 120 mg % glucose | olive |
| 180 mg % glucose and more | blue-green with increasing color depth |

In the case of the investigation of the blood of 53 diabetic patients in which the reaction colors were measured with a test strip photometer, there was obtained, in comparison with glucose determinations carried out by the hexokinase method, a correlation coefficient (r) of 0.9857. The standard deviation (2s) was ± 15 mg % glucose. Practically the same results were obtained ($r = 0.982$; $2s = \pm 17$ mg) with a test film made from the following components:

| | | |
|---|---|---|
| polyvinyl acetate dispersion (Propiofan 70 D) | | 45.0 g |
| 1.85 % solution of sodium alginate in 0.5 M phosphate buffer of pH 6.5 | | 35.0 g |
| ammonium perfluorooctanoate (Fluorad FC 126) dissolved in 10 ml water | | 1.0 g |
| glucose oxidase (62.4 u/mg) | dissolved in 10 ml water | 0.19 g |
| peroxidase (100 U/mg) | | 0.16 g |
| colanyl yellow HR | | 0.02 g |
| o-tolidine | | 0.5 g |
| 9-($\gamma$-aminopropyl)-3-aminocarbazole dihydrochloride | dissolved in 20 ml methanol | 0.026 g |

Example 4

Test paper for the detection of glucose in urine.

Filter paper (Schleicher & Schull No. 597 NF) was impregnated with a solution of the following composition and dried at 50°C:

| | | |
|---|---|---|
| 1M citrate buffer of pH 5 | | 50.0 ml |
| polyvinyl-pyrrolidone (average M.W. 12,000) | | 0.1 g |
| polyvinyl-pyrrolidone (average M.W. 40,000) | | 0.1 g |
| 9-($\gamma$-aminopropyl)-3-aminocarbazole dihydrochloride | | 3.12 g |
| glucose oxidase (104 U/mg) | | 0.3 g |
| peroxidase (63 U/mg) | | 0.06 g |
| water | ad | 100.0 ml |

The test paper reacted with glucose-containing urine with pink to violet-brown color shades. Urines of different origin, as well as acetoacetate-containing urines, all with the same glucose concentration, did not show any noteworthy deviations in the color shade obtained. A test paper with the same composition except that, instead of 9-($\gamma$-aminopropyl)-3-aminocarbazole dihydrochloride, it contained 3.0 g o-tolidine, reacted with these urines to give considerably differing color shades.

Disturbance-free reactions were also obtained with a test paper which had been produced in the following manner:

Filter paper (Schleicher & Schull No. 2312) was impregnated with a solution of 6.25 g 9-($\gamma$-aminopropyl-3-aminocarbazole dihydrochloride in 100 ml water and dried at 50°C. The paper pre-treated in this manner was then further impregnated with a solution of the following composition:

| | | |
|---|---|---|
| glucose oxidase (104 U/mg) | 0.39 | g |
| peroxide (63 U/mg) | 0.06 | g |
| polyoxyethylene sorbitan monolaurate (Tween 20) | 0.2 | g |
| 0.25M phosphate buffer of pH 5.0 ad | 100.0 | ml |

It will be understood that the foregoing specification and examples are illustrative but not limitative of the present invention inasmuch as other embodiments within the spirit and scope of the invention will suggest themselves to those skilled in the art.

What is claimed is:

1. Diagnostic test composition for the enzymatic detection of glucose containing 9-($\gamma$-aminopropyl)-3-aminocarbazole or salts thereof on a film or absorbent carrier.

2. Test composition as claimed in claim 1 in the enzymatic determination of glucose comprising 9-($\gamma$-aminopropyl)-3-aminocarbazole and a glucose indicator.

3. Test composition as claimed in claim 2 wherein said glucose indicator is a mixture of glucose oxidase, peroxidase and o-tolidine.

4. Test composition as claimed in claim 1 in the form of a test film having the reagents incorporated thereinto.

5. Test composition as claimed in claim 1 in the form of a test strip comprising an absorbent carrier.

6. Test composition as claimed in claim 4 wherein said test film is produced by mixing the test reagents with a synthetic resin dispersion and adding a thickening or a swelling agent thereto.

7. Test composition as claimed in claim 6 wherein said test films are produced by dissolving the 9-($\gamma$-aminopropyl)-3-aminocarbazole and as the glucose indicator, o-tolidine, in an organic solvent; mixing the remaining test reagent components in water; and mixing both of the resulting solutions into said synthetic resin dispersion.

8. Test composition as claimed in claim 4 consisting essentially of:
9-($\gamma$-aminopropyl)-3-aminocarbazole,
glucose oxidase
peroxidase,
o-tolidine,
a buffer,
a swelling agent, and
a wetting agent,
mixed into a synthetic resin dispersion.

9. Test composition as claimed in claim 5 consisting essentially of:
9-($\gamma$-aminopropyl)-3-aminocarbazole,
glucose oxidase,
peroxidase,
a buffer,
a wetting agent, and
a thickening agent,
sorbed onto the test paper.

10. Test strip as claimed in claim 5 wherein at least a portion of the strip is surface coated with the reagent mass.

11. Diagnostic test composition as claimed in claim 1 also containing an oxidation indicator.

12. Diagnostic test composition as claimed in claim 11 wherein said oxidation indicator is o-tolidine.

* * * * *